US005951524A

United States Patent [19]
Enriquez

[11] Patent Number: 5,951,524

[45] Date of Patent: Sep. 14, 1999

[54] GUARD AND HOLDER FOR VARIOUS SIZED TUBES

[76] Inventor: Oscar Enriquez, 800 Whitehall, Pflugerville, Tex. 78660

[21] Appl. No.: 09/197,591

[22] Filed: Nov. 23, 1998

[51] Int. Cl.$^{6}$ .................... A61M 5/32

[52] U.S. Cl. .................... 604/192; 604/263

[58] Field of Search .................... 604/192, 187, 604/110, 263; 206/365, 366

[56] References Cited

U.S. PATENT DOCUMENTS

| | | |
|---|---|---|
| 4,573,975 | 3/1986 | Frist et al. . |
| 4,840,618 | 6/1989 | Marvel . |
| 4,981,476 | 1/1991 | Aichlmayr et al. . |
| 4,982,850 | 1/1991 | Mears . |
| 5,061,248 | 10/1991 | Sacco . |
| 5,217,694 | 6/1993 | Gibler et al. . |
| 5,314,413 | 5/1994 | McCowan et al. . |
| 5,330,439 | 7/1994 | Jackson . |
| 5,375,716 | 12/1994 | Rubin et al. . |
| 5,579,928 | 12/1996 | Anukwuem . |
| 5,624,404 | 4/1997 | Fisler . |
| 5,707,861 | 1/1998 | Sherman et al. . |

*Primary Examiner*—John D. Yasko
*Attorney, Agent, or Firm*—Joseph F. Long

[57] ABSTRACT

A transparent flat circular rigid plate a minimum of three inches in diameter with a minimum of four holes clustered around a central point and sized to closely fit vacutainer tubes with hole cover plates rotatably installed to cover any unused holes. With one or more vacutainer tubes installed the tubes may be held firmly in one hand underneath the plate thereby enabling a user to insert a hypodermic needle to fill a vacutainer tube and remove the hypodermic needle without lifting the vacutainer tube so as to be able to fill all installed vacutainer tubes safely and with minimum effort.

3 Claims, 3 Drawing Sheets

GUARD AND HOLDER FOR VARIOUS SIZED TUBES

BACKGROUND OF THE INVENTION

Vacutainer® tubes are tubes commonly used in medical laboratories; these tubes are of differing sizes; evacuated to pull in the proper amount of liquid for a particular test and closed with a septum or stopper that may be pierced with a hypodermic needle to pull the proper amount of liquid from the hypodermic needle for the particular test and seal the vacutainer® tube upon withdrawal of the hypodermic needle. A guard to allow the technician to safely use the tubes by prevention of accidental self injection is of critical interest to the technician. The objectives of this invention are to provide a safe, simple economical guard and tube holder that the technician may use with the minimum effort and the maximum efficiency. Preferably the unit should be simple enough that a technician may carry several in a pocket and cheap enough to be a throw-away item while providing the necessary protection.

There are several patents in the prior art that are intended to protect the technician from accidental needle sticks while transferring fluids to tube containers. We find no prior art that adequately fulfills the objectives of our invention as outlined in these specifications and claims.

SUMMARY OF THE INVENTION

The invention comprises a tube holder and a safety guard to allow a technician to transfer liquid such as blood from a hypodermic needle through a plastic or rubber septum or through the stopper normally used to close vacutainer® tubes with a guard to prevent the technician from accidentally sticking his or her hand. The guard has a minimum of four holes sized to fit the particular tube for a particular test; the holes are centrally grouped to allow the technician to hold the tubes with a hand underneath the guard while using the hypodermic needle in the other hand.

The upper surface of the guard is roughened or has concentric grooves to prevent the needle from slipping off the edge of the guard.

There are four rotatable hole cover plates installed in the guard that the technician rotates to cover any unused holes. This is necessary since there are instances when less than four tests are run at one time and less than four tubes are needed.

DETAILED DESCRIPTION OF THE INVENTION

Figure 1:
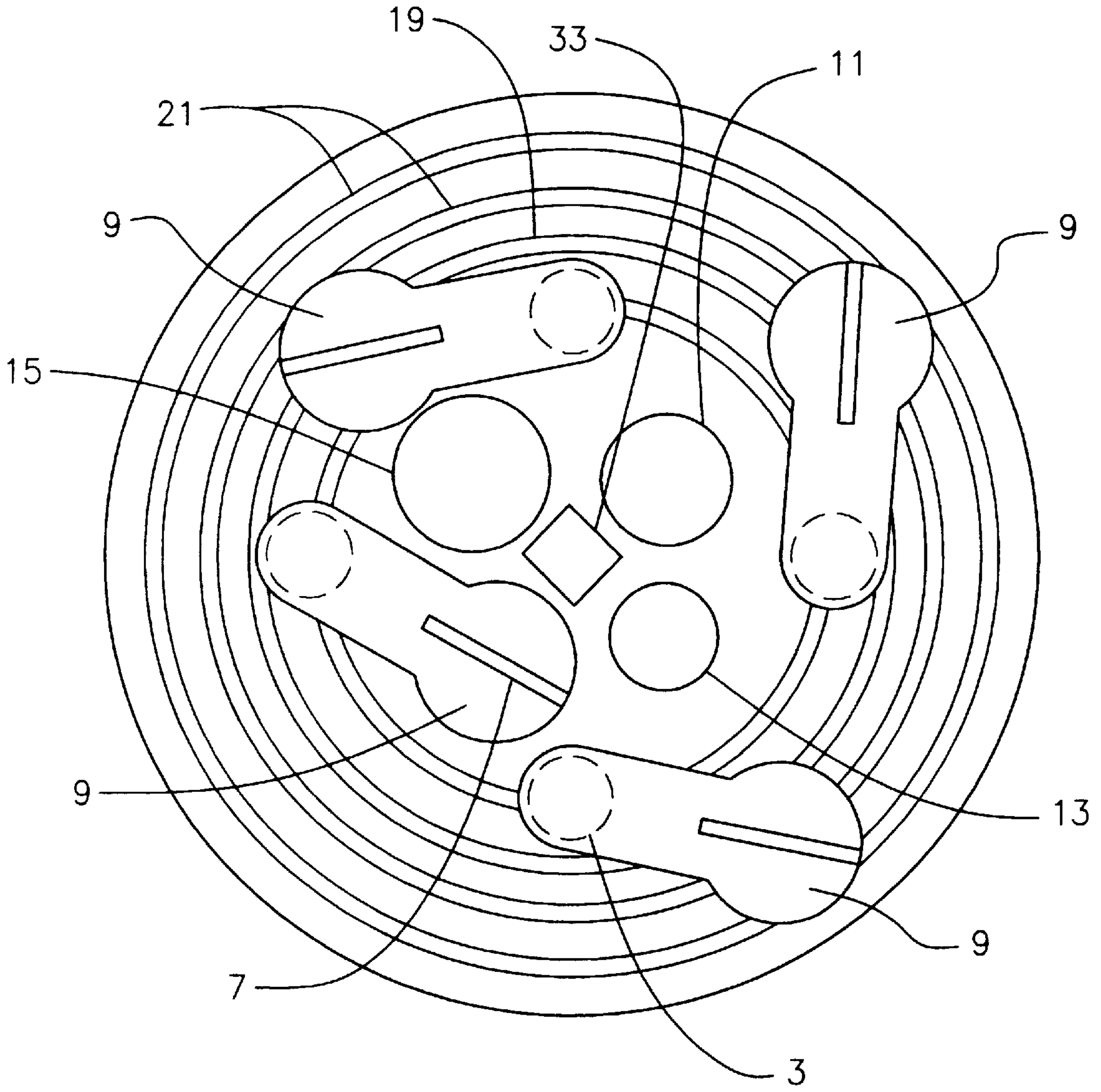
FIG. 1 shows a top view of the safety plate with one of four hole covers installed and all cover plates workably installed.

The invention may best be described from the drawings. FIG. 1 shows a top view of the guard and holder 1 with holes 11, 13 17, and 15; these are preferably sized to be 0.4325, 0.3940, 0.4949, and 0.4949 inches respectively but these holes may be sized to fit any tube that comes into use. Preferably the holes fit the tubes closely. Hole cover plate 9 with thumb latch 7 is shown installed in one of the four cover plate holes 3 to cover the hole for the hole 17 for one of the tubes. The other cover plates are shown installed and ready for use. As shown the guard and holder 1 is set to receive three tubes. A first safety groove 19 connects the holes 3 and multiple concentric safety grooves 21 that may be about five hundredths of an inch deep and one tenth of an in inch wide are used to prevent a needle from slipping off the guard as the technician is trying to insert a needle through the stopper of a tube in the tube holder. The size of the grooves is not critical. A rough surface or even a soft surface could be used for the purpose of preventing the needle from slipping off the guard 1. A raised stop, preferably square, 33 may be used to prevent the cover plate from moving too far as the user pushes the plate into the in-use position using cover plate thumb latch 7.

Figure 2:
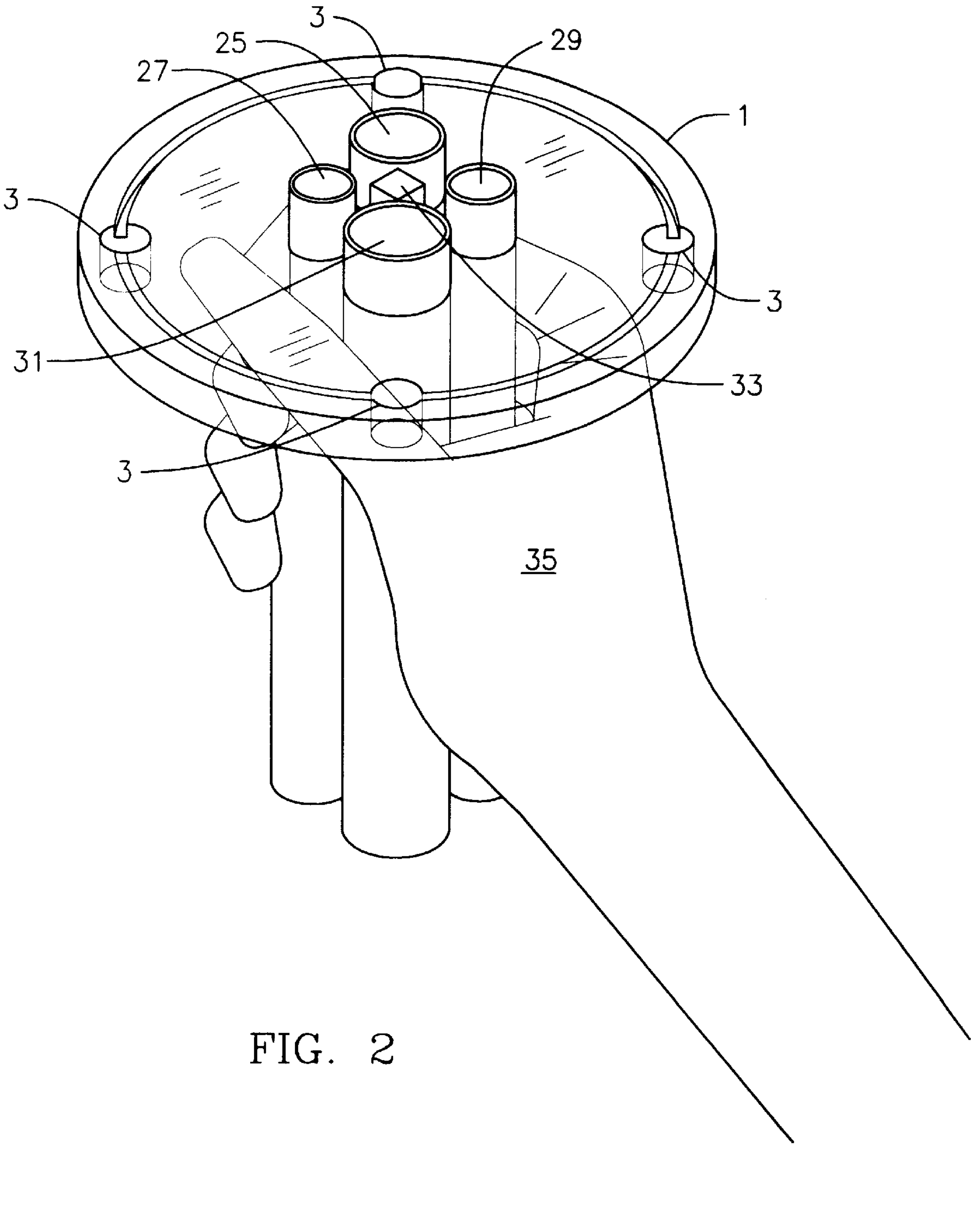
FIG. 2 Shows a three dimensional view to indicate how all the tubes may be held in one guarded hand.

FIG. 2 shows a three dimensional view of holder and guard 1 with vacutainer tubes 25, 27, 29, and 31 installed therein indicating how hand 35 may firmly hold all tubes and be guarded from accidental injection. Note that all four tubes may be firmly held in one hand allowing the technician to safely push a hypodermic needle through a stopper in the vacutainer tube and also to remove the hypodermic from one tube and insert in another tube without removal of the hypodermic needle causing a tube to lift out of the holder. This greatly facilitates the technician's work when one blood sample is to be measured out into separate tubes for differing tests. Hole cover plates 9, FIG. 1 are normally installed but are not shown in the interest of drawing clarity. Other numbers on the drawing are as previously discussed.

Figure 3:
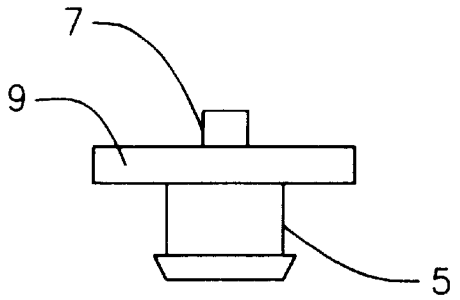
FIG. 3 Shows end view of the hole cover plate.

FIG. 3 shows an end view of hole cover plate 9 with thumb latch 7 and protrusion 5 with a snap ring that rotatably holds the hole cover in place when pushed through hole 3, FIG. 1.

Figure 4:
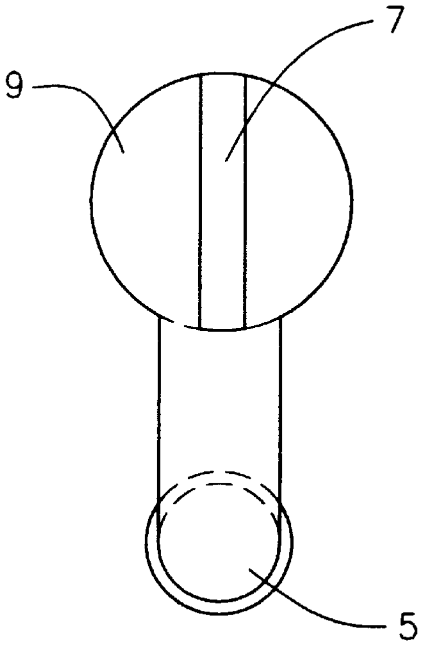
FIG. 4 Top view of hole cover plate.

FIG. 4 shows a top view of cover plate 9 with thumb latch 7 with the larger end being about one inch in diameter and the smaller end being about three tenths of an inch in width.

Figure 5:
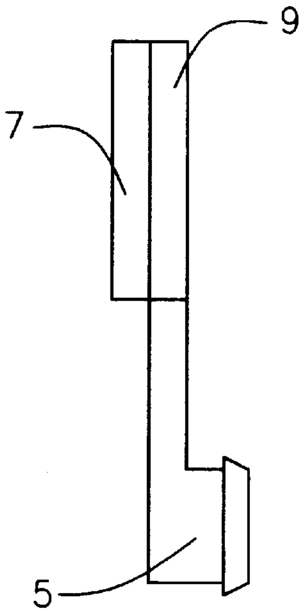
FIG. 5 Side view of hole cover plate.

FIG. 5 shows a side view of hole cover plate 9 with thumb latch 7 and projection 5 sized to rotatably snap into one of holes 3, FIG. 2.

What is claimed is:

1. A holder and guard for various sizes of vacutainer®tubes comprising a) a transparent circular plate a minimum of three inches in diameter, said circular plate having a minimum of four holes varying from about one third to one half inch in diameter clustered around a center point so as to be less than one inch apart; said circular plate also having four holes spaced at 90 degree angles encircling said minimum of said four holes around said center point;

b) a minimum of four flat hole cover plates having a first circular end a minimum of about one inch in diameter and having a rotatable protrusion on a second end sized to rotatably fit into one of said four holes in said four holes spaced ninety degrees apart in said circular plate thereby allowing said hole cover plates to be rotated to cover any unused holes in said circular plate.

2. A holder and guard for vacutainer®tubes as in claim 1 further comprising a means to prevent an in-use hypodermic needle point from slipping off said holder and guard.

3. A holder and guard as in claim 2 wherein said means to prevent an in-use hypodermic needle point from slipping off said holder and guard is a minimum of one circular groove about one tenth of an inch wide and five hundredths of an inch deep on an upper surface of said holder and guard.

* * * * *